(12) United States Patent
Rubinfeld

(10) Patent No.: US 11,464,673 B1
(45) Date of Patent: Oct. 11, 2022

(54) MULTIFACTORIAL DRY EYE TREATMENT METHOD

(71) Applicant: Eric Rubinfeld, Yonkers, NY (US)

(72) Inventor: Eric Rubinfeld, Yonkers, NY (US)

( * ) Notice: Subject to any disclaimer, the term of this patent is extended or adjusted under 35 U.S.C. 154(b) by 0 days.

(21) Appl. No.: 17/846,687

(22) Filed: Jun. 22, 2022

Related U.S. Application Data

(60) Provisional application No. 63/364,781, filed on May 16, 2022.

(51) Int. Cl.
| | |
|---|---|
| A61F 9/00 | (2006.01) |
| A61N 5/06 | (2006.01) |
| A61F 7/08 | (2006.01) |
| A61K 31/245 | (2006.01) |
| A61K 35/50 | (2015.01) |
| A61F 13/12 | (2006.01) |
| A61F 7/02 | (2006.01) |
| A61K 31/5383 | (2006.01) |
| A61F 7/00 | (2006.01) |

(52) U.S. Cl.
CPC ............. *A61F 9/0008* (2013.01); *A61F 7/02* (2013.01); *A61F 7/08* (2013.01); *A61F 13/124* (2013.01); *A61K 31/245* (2013.01); *A61K 31/5383* (2013.01); *A61K 35/50* (2013.01); *A61N 5/0613* (2013.01); *A61F 2007/0004* (2013.01); *A61F 2007/0234* (2013.01); *A61F 2007/0242* (2013.01); *A61N 2005/0626* (2013.01); *A61N 2005/0654* (2013.01); *A61N 2005/0663* (2013.01)

(58) Field of Classification Search
CPC .. A61F 9/0008; A61F 7/02; A61F 7/08; A61F 13/124; A61F 2007/0004; A61F 2007/0234; A61F 2007/0242; A61K 31/245; A61K 31/5383; A61K 35/50; A61N 5/0613; A61N 2005/0626; A61N 2005/0654; A61N 2005/0663
USPC ......................................................... 604/20
See application file for complete search history.

*Primary Examiner* — Aaron F Roane
(74) *Attorney, Agent, or Firm* — RC Trademark Company, LLC

(57) ABSTRACT

The present embodiments relate to a method of treating dry eyes. The method includes a plurality of visits to an eye doctor with each even numbered visit focused on a first eye and each odd numbered visit focused on a second eye. The plurality of visits comprises use of intense pulsed light ("IPL") therapy, low level light therapy, an ocular nebulizer, dehydrated amniotic membranes, biologic eye drops, advanced lubricants, eyelid debridement, meibomian gland imaging and a slit lamp.

2 Claims, 1 Drawing Sheet

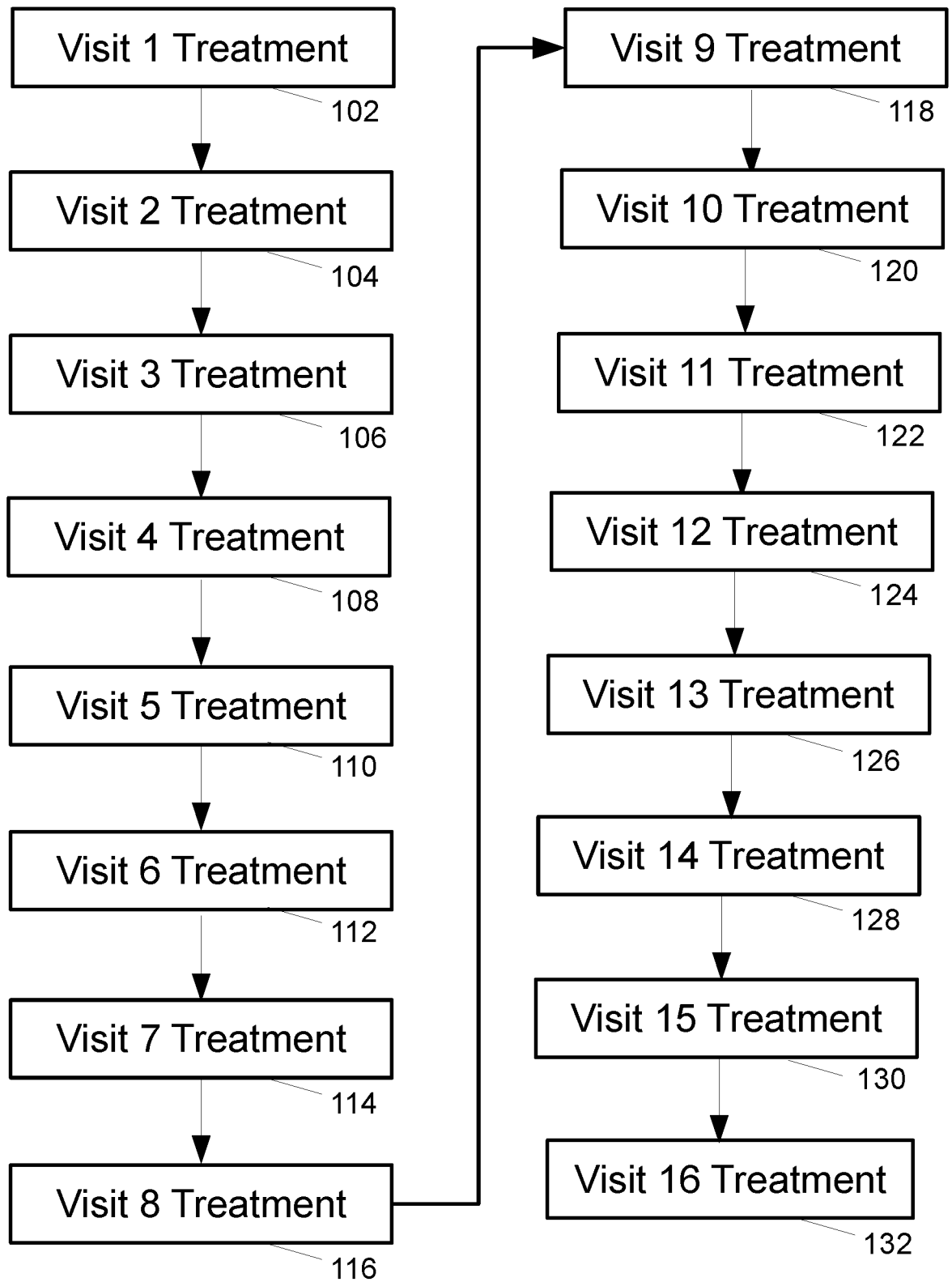

MULTIFACTORIAL DRY EYE TREATMENT METHOD

BACKGROUND

Due to the COVID-19 pandemic, many people are required to wear masks (e.g., N95, KN95, etc.) for their job or employment. As these masks often don't make a tight fit, air is forced upwards toward the wearer's eyes causing the eyes to dry out. Since a worker may be required to wear a mask for extended hours, dry eyes issues have become increasingly common due to the COVID-19 pandemic.

Dry eye syndrome (DES), also known as keratoconjunctivitis sicca (KCS), is a condition of having dry eyes with multifactorial causes. Amongst those causes are meibomian gland disease (MGD) and blepharitis which compromise the integrity of the tear film. Long term tear film issues can lead to corneal limbal stem cell deficiency, conjunctival hyperemia, corneal epithelial defects, conjunctivalization of the cornea, corneal neovascularization, and corneal endothelial dystrophy. Subjectively, the patient can experience the following symptoms: irritation, redness, eye fatigued, transient blurred vision, tearing to name a few. Therefore, a method of relieving dry eyes is desirable.

SUMMARY

The embodiments described relate to a method of treating dry eyes. The method includes a plurality of visits to an eye doctor with each even numbered visit focused on a first eye and each odd numbered visit focused on a second eye. The plurality of visits comprises use of intense pulsed light ("IPL") therapy, low level light therapy, an ocular nebulizer, dehydrated amniotic membranes, biologic eye drops, advanced lubricants, eyelid debridement, meibomian gland imaging and a slit lamp.

BRIEF DESCRIPTION OF THE DRAWING

FIG. 1 illustrates a method in accordance with some embodiments.

DETAILED DESCRIPTION

The following is a method associated with the multifactorial treatment of dry eyes and the associated clinical findings found at different stages of advancement of the disease. In some embodiments, the method may comprise an eight-week cycle of visits to a medical professional (e.g., eye doctor) comprising two visits per week. The first visit may be associated with treatment of a right eye and the second visit may be associated with treatment of a left eye. However, the order of eye treatment may be reversed.

The method described herein may treat the underlying cause of dry eye and the associated abnormalities to the ocular surface that develop as the disease progresses. The method may comprise a plurality of visits with an eye doctor and the associated treatments/steps may be useful in providing relief of dry eyes. The method described herein may be performed for an 8-week cycle that continues until both objective and subjective improvement in the patient occurs based on slit lamp findings and the patient reported decrease in symptoms. The method requires a series of visits with each visit comprising a specific treatment plan. In some embodiments, a first treatment is for a right eye and a next treatment is for a left eye. This pattern of alternating subject eyes may continue through the entire treatment. In some embodiments, the method described herein comprises at least sixteen visits with each visit associated with a specific treatment. For example, a sixteen-visit plan is illustrated in FIG. 1. The sixteen-visit plan may include, but is not limited to, the following:

Visit 1 Treatment (See 102 of FIG. 1):

A. Intense Pulsed Light ("IPL") treatment where settings are determined by skin pigmentation, susceptibility to sun burn and level of meibomian gland dysfunction ("MGD").

B. A lid treatment of both eyes.

C. A low-level light therapy using a blue light (e.g., Eye Rescue™ Blue LLLT) for 10-20 minutes. In some embodiments, the therapy may last for 15 minutes.

D. A low-level light therapy using a blue light (e.g., Eye Rescue™ Red LLLT) for 10-20 minutes. In some embodiments, the therapy may last for 15 minutes.

E. A slit lamp examination of the eyes with photos taken of the eyes.

F. Meibomian gland expression. In this step, meibum may be expressed from meibomian glands to promote secretion of an oil or to clear a blockage. Expressing meibomian glands may be done via a plurality of tools different tools.

G. A single drop of proparacaine 1% may be instilled in a subject eye.

H. A dehydrated amniotic membrane (e.g., 8 mm) may be placed on either center of a subject eye cornea or on a concave surface of a bandage contact lens (or collagen membrane). If the amniotic membrane is placed directly on the cornea, the bandage contact lens or collagen membrane may be paced on top of the amniotic membrane and inserted on the cornea.

I. A patient removes the bandage contact lens themselves in eight hours or returns to the office the same day or next morning for a doctor to remove. If a dissolvable collagen membrane is used, the patient may leave the amniotic and collagen membrane in their eye and it will dissolve on its own within 24 hours.

J. Patient is given Ofloxacin 0.3% to be instilled into a subject eye twice per day for 4 days.

K. Patient is given a non-preserved lubricant (e.g., Optase) to use at least twice per day (or more if needed) in both eyes and a biologic eye drop (e.g., RegenerEyes) is used, at least, twice per day in both eyes. These non-preserved lubricant drops patient continues daily until the doctor concludes or amends treatment program.

L. Patient is given a home use dry eye mask (e.g., a microwaveable mask) to use once per day to help melt/heat the impacted meibomian glands in their lids. This home treatment continues daily until the doctor concludes or amends treatment program.

Visit 2 treatment (See 104 of FIG. 1):

A. Intense Pulsed Light ("IPL") treatment where settings are determined by skin pigmentation, susceptibility to sun burn and level of meibomian gland dysfunction ("MGD").

B. A lid treatment of both eyes.

C. A low-level light therapy using a blue light (e.g., Eye Rescue™ Blue LLLT) for 10-20 minutes. In some embodiments, the therapy may last for 15 minutes.

D. A low-level light therapy using a blue light (e.g., Eye Rescue™ Red LLLT) for 10-20 minutes. In some embodiments, the therapy may last for 15 minutes.

E. A slit lamp examination of the eyes with photos taken of the eyes.

F. Meibomian gland expression. In this step, meibum may be expressed from meibomian glands to promote secretion of an oil or to clear a blockage. Expressing meibomian glands may be done via a plurality of tools different tools.

G. A single drop of proparacaine 1% may be instilled in a subject eye.

H. A dehydrated amniotic membrane (e.g., 8 mm) may be placed on either center of a subject eye cornea or on a concave surface of a bandage contact lens (or collagen membrane). If the amniotic membrane is placed directly on the cornea, the bandage contact lens or collagen membrane may be paced on top of the amniotic membrane and inserted on the cornea.

I. A patient removes the bandage contact lens themselves in eight hours or returns to the office the same day or next morning for a doctor to remove. If a dissolvable collagen membrane is used, the patient may leave the amniotic and collagen membrane in their eye and it will dissolve on its own within 24 hours.

J. Patient is given Ofloxacin 0.3% to be instilled into a subject eye twice per day for 4 days.

The patient is instructed to return in 48-72 hours to repeat the above-mentioned procedure.

Visit 3 treatment staring on the second week. (See 106 of FIG. 1):

A. Intense Pulsed Light ("IPL") treatment where settings are determined by skin pigmentation, susceptibility to sun burn and level of meibomian gland dysfunction ("MGD").

B. A lid treatment of both eyes.

C. A low-level light therapy using a blue light (e.g., Eye Rescue™ Blue LLLT) for 10-20 minutes. In some embodiments, the therapy may last for 15 minutes.

D. A low-level light therapy using a blue light (e.g., Eye Rescue™ Red LLLT) for 10-20 minutes. In some embodiments, the therapy may last for 15 minutes.

E. A slit lamp examination of the eyes with photos taken of the eyes.

F. Meibomian gland expression. In this step, meibum may be expressed from meibomian glands to promote secretion of an oil or to clear a blockage. Expressing meibomian glands may be done via a plurality of tools different tools.

G. A single drop of proparacaine 1% may be instilled in a subject eye.

H. A dehydrated amniotic membrane (e.g., 8 mm) may be placed on either center of a subject eye cornea or on a concave surface of a bandage contact lens (or collagen membrane). If the amniotic membrane is placed directly on the cornea, the bandage contact lens or collagen membrane may be paced on top of the amniotic membrane and inserted on the cornea.

I. A patient removes the bandage contact lens themselves in eight hours or returns to the office the same day or next morning for a doctor to remove. If a dissolvable collagen membrane is used, the patient may leave the amniotic and collagen membrane in their eye and it will dissolve on its own within 24 hours.

J. Patient is given Ofloxacin 0.3% to be instilled into a subject eye twice per day for 4 days.

K. Patient is given a non-preserved lubricant (e.g., Optase) to use at least twice per day (or more if needed) in both eyes and a biologic eye drop (e.g., RegenerEyes) is used, at least, twice per day in both eyes. These non-preserved lubricant drops patient continues daily until the doctor concludes or amends treatment program.

After the first two treatments, the patient may be scheduled to return for two visits the following week starting with the right eye (or left eye)):

Visit 4 treatment ($2^{nd}$ week-See 108 of FIG. 1)

A. Intense Pulsed Light ("IPL") treatment where settings are determined by skin pigmentation, susceptibility to sun burn and level of meibomian gland dysfunction ("MGD").

B. A lid treatment of both eyes.

C. A low-level light therapy using a blue light (e.g., Eye Rescue™ Blue LLLT) for 10-20 minutes. In some embodiments, the therapy may last for 15 minutes.

D. A low-level light therapy using a blue light (e.g., Eye Rescue™ Red LLLT) for 10-20 minutes. In some embodiments, the therapy may last for 15 minutes.

E. A slit lamp examination of the eyes with photos taken of the eyes.

F. Meibomian gland expression. In this step, meibum may be expressed from meibomian glands to promote secretion of an oil or to clear a blockage. Expressing meibomian glands may be done via a plurality of tools different tools.

G. A single drop of proparacaine 1% may be instilled in a subject eye.

H. A dehydrated amniotic membrane (e.g., 8 mm) may be placed on either center of a subject eye cornea or on a concave surface of a bandage contact lens (or collagen membrane). If the amniotic membrane is placed directly on the cornea, the bandage contact lens or collagen membrane may be paced on top of the amniotic membrane and inserted on the cornea.

I. A patient removes the bandage contact lens themselves in eight hours or returns to the office the same day or next morning for a doctor to remove. If a dissolvable collagen membrane is used, the patient may leave the amniotic and collagen membrane in their eye and it will dissolve on its own within 24 hours.

J. Patient is given Ofloxacin 0.3% to be instilled into a subject eye twice per day for 4 days.

Patient scheduled to return for 2 visits the following week.

Visit 5 treatment ($3^{rd}$ week-See 110 of FIG. 1)

A. Use of an ocular nebulizer for 10-20 minutes. In some embodiments, the ocular nebulizer is used for 15 minutes.

B. Slit lamp examination with photos of the subject eye.

C. A single drop of proparacaine 1% may be instilled in a subject eye.

D. A dehydrated amniotic membrane (e.g., 8 mm) may be placed on either center of a subject eye cornea or on a concave surface of a bandage contact lens (or collagen membrane). If the amniotic membrane is placed directly on the cornea, the bandage contact lens or collagen membrane may be paced on top of the amniotic membrane and inserted on the cornea.

E. A patient removes the bandage contact lens themselves in eight hours or returns to the office the same day or next morning for a doctor to remove. If a dissolvable collagen membrane is used, the patient may leave the amniotic and collagen membrane in their eye and it will dissolve on its own within 24 hours.

F. Patient is given Ofloxacin 0.3% to be instilled into a subject eye twice per day for 4 days.

Patient is instructed to return in 48-72 hours for their left eye treatment.

Visit 6 treatment ($3^{rd}$ week-See 112 of FIG. 1)

A. Use of an ocular nebulizer for 10-20 minutes. In some embodiments, the ocular nebulizer is used for 15 minutes.

B. Slit lamp examination with photos of the subject eye.

C. A single drop of proparacaine 1% may be instilled in a subject eye.

D. A dehydrated amniotic membrane (e.g., 8 mm) may be placed on either center of a subject eye cornea or on a concave surface of a bandage contact lens (or collagen membrane). If the amniotic membrane is placed directly on the cornea, the bandage contact lens or collagen membrane may be paced on top of the amniotic membrane and inserted on the cornea.

E. A patient removes the bandage contact lens themselves in eight hours or returns to the office the same day or next morning for a doctor to remove. If a dissolvable collagen membrane is used, the patient may leave the amniotic and collagen membrane in their eye and it will dissolve on its own within 24 hours.

F. Patient is given Ofloxacin 0.3% to be instilled into a subject eye twice per day for 4 days.

F. Patient scheduled to return for 2 visits the following week.

Visit 7th treatment (4th week-See 114 of FIG. 1)

A. Use of an ocular nebulizer for 10-20 minutes. In some embodiments, the ocular nebulizer is used for 15 minutes.

B. Slit lamp examination with photos of the subject eye.

C. A single drop of proparacaine 1% may be instilled in a subject eye.

D. A dehydrated amniotic membrane (e.g., 8 mm) may be placed on either center of a subject eye cornea or on a concave surface of a bandage contact lens (or collagen membrane). If the amniotic membrane is placed directly on the cornea, the bandage contact lens or collagen membrane may be paced on top of the amniotic membrane and inserted on the cornea.

E. A patient removes the bandage contact lens themselves in eight hours or returns to the office the same day or next morning for a doctor to remove. If a dissolvable collagen membrane is used, the patient may leave the amniotic and collagen membrane in their eye and it will dissolve on its own within 24 hours.

F. Patient is given Ofloxacin 0.3% to be instilled into a subject eye twice per day for 4 days.

F. Patient is instructed to return in 48-72 hours for another treatment.

Visit 8th treatment (4th week-See 116 of FIG. 1)

A. Use of an ocular nebulizer for 10-20 minutes. In some embodiments, the ocular nebulizer is used for 15 minutes.

B. Slit lamp examination with photos of the subject eye.

C. A single drop of proparacaine 1% may be instilled in a subject eye.

D. A dehydrated amniotic membrane (e.g., 8 mm) may be placed on either center of a subject eye cornea or on a concave surface of a bandage contact lens (or collagen membrane). If the amniotic membrane is placed directly on the cornea, the bandage contact lens or collagen membrane may be paced on top of the amniotic membrane and inserted on the cornea.

E. A patient removes the bandage contact lens themselves in eight hours or returns to the office the same day or next morning for a doctor to remove. If a dissolvable collagen membrane is used, the patient may leave the amniotic and collagen membrane in their eye and it will dissolve on its own within 24 hours.

F. Patient is given Ofloxacin 0.3% to be instilled into a subject eye twice per day for 4 days. After 4 days no further use of Ofloxacin for future visits.

Patient scheduled to return for 2 visits the following week.

Visit 9th treatment (5$^{th}$ week-See 118 of FIG. 1):

A. Intense Pulsed Light ("IPL") treatment where settings are determined by skin pigmentation, susceptibility to sun burn and level of meibomian gland dysfunction ("MGD").

B. A low-level light therapy using a blue light (e.g., Eye Rescue™ Blue LLLT) for 10-20 minutes. In some embodiments, the therapy may last for 15 minutes.

C. A low-level light therapy using a blue light (e.g., Eye Rescue™ Red LLLT) for 10-20 minutes. In some embodiments, the therapy may last for 15 minutes.

D. A slit lamp examination of the eyes with photos taken of the eyes.

E. Meibomian gland expression. In this step, meibum may be expressed from meibomian glands to promote secretion of an oil or to clear a blockage. Expressing meibomian glands may be done via a plurality of tools different tools.

F. A single drop of proparacaine 1% may be instilled in a subject eye.

G. A dehydrated amniotic membrane (e.g., 8 mm) may be placed on either center of a subject eye cornea or on a concave surface of a bandage contact lens (or collagen membrane). If the amniotic membrane is placed directly on the cornea, the bandage contact lens or collagen membrane may be paced on top of the amniotic membrane and inserted on the cornea.

H. A patient removes the bandage contact lens themselves in eight hours or returns to the office the same day or next morning for a doctor to remove. If a dissolvable collagen membrane is used, the patient may leave the amniotic and collagen membrane in their eye and it will dissolve on its own within 24 hours.

Patient scheduled to return in 48-72 hours for another eye treatment.

Visit 10th treatment (5$^{th}$ week-See 120 of FIG. 1):

A. A low-level light therapy using a blue light (e.g., Eye Rescue™ Blue LLLT) for 10-20 minutes. In some embodiments, the therapy may last for 15 minutes.

B. A low-level light therapy using a blue light (e.g., Eye Rescue™ Red LLLT) for 10-20 minutes. In some embodiments, the therapy may last for 15 minutes.

C. A slit lamp examination of the eyes with photos taken of the eyes.

D. Meibomian gland expression. In this step, meibum may be expressed from meibomian glands to promote secretion of an oil or to clear a blockage. Expressing meibomian glands may be done via a plurality of tools different tools.

E. A single drop of proparacaine 1% may be instilled in a subject eye.

F. A dehydrated amniotic membrane (e.g., 8 mm) may be placed on either center of a subject eye cornea or on a concave surface of a bandage contact lens (or collagen membrane). If the amniotic membrane is placed directly on the cornea, the bandage contact lens or collagen membrane may be paced on top of the amniotic membrane and inserted on the cornea.

G. A patient removes the bandage contact lens themselves in eight hours or returns to the office the same day or next morning for a doctor to remove. If a dissolvable collagen membrane is used, the patient may leave the amniotic and collagen membrane in their eye and it will dissolve on its own within 24 hours.

Patient scheduled to return for 2 visits the following week.

Visit 11th treatment (6$^{th}$ week-See 122 of FIG. 1):

A. A. A low-level light therapy using a blue light (e.g., Eye Rescue™ Blue LLLT) for 10-20 minutes. In some embodiments, the therapy may last for 15 minutes.

B. A low-level light therapy using a blue light (e.g., Eye Rescue™ Red LLLT) for 10-20 minutes. In some embodiments, the therapy may last for 15 minutes.

C. A slit lamp examination of the eyes with photos taken of the eyes.

D. Meibomian gland expression. In this step, meibum may be expressed from meibomian glands to promote secretion of an oil or to clear a blockage. Expressing meibomian glands may be done via a plurality of tools different tools.

E. A single drop of proparacaine 1% may be instilled in a subject eye.

F. A dehydrated amniotic membrane (e.g., 8 mm) may be placed on either center of a subject eye cornea or on a concave surface of a bandage contact lens (or collagen membrane). If the amniotic membrane is placed directly on the cornea, the bandage contact lens or collagen membrane may be paced on top of the amniotic membrane and inserted on the cornea.

G. A patient removes the bandage contact lens themselves in eight hours or returns to the office the same day or next morning for a doctor to remove. If a dissolvable collagen membrane is used, the patient may leave the amniotic and collagen membrane in their eye and it will dissolve on its own within 24 hours.

Patient scheduled to return in 48-72 hours for their left eye treatment.

Visit 12th treatment (6$^{th}$ week-See 124 of FIG. 1):

A. A low-level light therapy using a blue light (e.g., Eye Rescue™ Blue LLLT) for 10-20 minutes. In some embodiments, the therapy may last for 15 minutes.

B. A low-level light therapy using a blue light (e.g., Eye Rescue™ Red LLLT) for 10-20 minutes. In some embodiments, the therapy may last for 15 minutes.

C. A slit lamp examination of the eyes with photos taken of the eyes.

D. Meibomian gland expression. In this step, meibum may be expressed from meibomian glands to promote secretion of an oil or to clear a blockage. Expressing meibomian glands may be done via a plurality of tools different tools.

E. A single drop of proparacaine 1% may be instilled in a subject eye.

F. A dehydrated amniotic membrane (e.g., 8 mm) may be placed on either center of a subject eye cornea or on a concave surface of a bandage contact lens (or collagen membrane). If the amniotic membrane is placed directly on the cornea, the bandage contact lens or collagen membrane may be paced on top of the amniotic membrane and inserted on the cornea.

G. A patient removes the bandage contact lens themselves in eight hours or returns to the office the same day or next morning for a doctor to remove. If a dissolvable collagen membrane is used, the patient may leave the amniotic and collagen membrane in their eye and it will dissolve on its own within 24 hours.

Patient scheduled to return for 2 visits the following week.

Visit 13 treatment (7th week-See 126 of FIG. 1)

A. Use of an ocular nebulizer for 10-20 minutes. In some embodiments, the ocular nebulizer is used for 15 minutes. In some embodiments a blephasteam eye steamer may be used.

B. Slit lamp examination with photos of the subject eye.

C. A single drop of proparacaine 1% may be instilled in a subject eye.

D. A dehydrated amniotic membrane (e.g., 8 mm) may be placed on either center of a subject eye cornea or on a concave surface of a bandage contact lens (or collagen membrane). If the amniotic membrane is placed directly on the cornea, the bandage contact lens or collagen membrane may be paced on top of the amniotic membrane and inserted on the cornea.

E. A patient removes the bandage contact lens themselves in eight hours or returns to the office the same day or next morning for a doctor to remove. If a dissolvable collagen membrane is used, the patient may leave the amniotic and collagen membrane in their eye and it will dissolve on its own within 24 hours.

F. Patient is instructed to return in 48-72 hours for their left eye treatment.

Visit 14 treatment (7$^{rd}$ week-See 128 of FIG. 1)

A. Use of an ocular nebulizer for 10-20 minutes. In some embodiments, the ocular nebulizer is used for 15 minutes. In some embodiments a blephasteam eye steamer may be used.

B. Slit lamp examination with photos of the subject eye.

C. A single drop of proparacaine 1% may be instilled in a subject eye.

D. A dehydrated amniotic membrane (e.g., 8 mm) may be placed on either center of a subject eye cornea or on a concave surface of a bandage contact lens (or collagen membrane). If the amniotic membrane is placed directly on the cornea, the bandage contact lens or collagen membrane may be paced on top of the amniotic membrane and inserted on the cornea.

E. A patient removes the bandage contact lens themselves in eight hours or returns to the office the same day or next morning for a doctor to remove. If a dissolvable collagen membrane is used, the patient may leave the amniotic and collagen membrane in their eye and it will dissolve on its own within 24 hours.

F. Patient scheduled to return for 2 visits the following week.

Visit 15th treatment (8th week-See 130 of FIG. 1)

A. Use of an ocular nebulizer for 10-20 minutes. In some embodiments, the ocular nebulizer is used for 15 minutes. In some embodiments a blephasteam eye steamer may be used.

B. Slit lamp examination with photos of the subject eye.

C. A single drop of proparacaine 1% may be instilled in a subject eye.

D. A dehydrated amniotic membrane (e.g., 8 mm) may be placed on either center of a subject eye cornea or on a concave surface of a bandage contact lens (or collagen membrane). If the amniotic membrane is placed directly on the cornea, the bandage contact lens or collagen membrane may be paced on top of the amniotic membrane and inserted on the cornea.

E. A patient removes the bandage contact lens themselves in eight hours or returns to the office the same day or next morning for a doctor to remove. If a dissolvable collagen membrane is used, the patient may leave the amniotic and collagen membrane in their eye and it will dissolve on its own within 24 hours.

Patient is instructed to return in 48-72 hours for their left eye treatment.

Visit 16th treatment (8th week-See 132 of FIG. 1)

A. Use of an ocular nebulizer for 10-20 minutes. In some embodiments, the ocular nebulizer is used for 15 minutes. In some embodiments a blephasteam eye steamer may be used.

B. Slit lamp examination with photos of the subject eye.

C. A single drop of proparacaine 1% may be instilled in a subject eye.

D. A dehydrated amniotic membrane (e.g., 8 mm) may be placed on either center of a subject eye cornea or on a concave surface of a bandage contact lens (or collagen membrane). If the amniotic membrane is placed directly on the cornea, the bandage contact lens or collagen membrane may be paced on top of the amniotic membrane and inserted on the cornea.

E. A patient removes the bandage contact lens themselves in eight hours or returns to the office the same day or next morning for a doctor to remove. If a dissolvable collagen membrane is used, the patient may leave the amniotic and collagen membrane in their eye and it will dissolve on its own within 24 hours.

F. Patient scheduled to return for 2 visits the following week and the above treatment protocol continues until subjective and objective clinical findings resolved.

This written description uses examples to disclose multiple embodiments, including the preferred embodiments, and also to enable any person skilled in the art to practice the invention, including making and using any devices or systems and performing any incorporated methods. Aspects from the various embodiments described, as well as other known equivalents for each such aspects, can be mixed and matched by one of ordinary skill in the art to construct additional embodiments and techniques in accordance with principles of this application.

Those in the art will appreciate that various adaptations and modifications of the above-described embodiments can be configured without departing from the scope and spirit of the claims. Therefore, it is to be understood that the claims may be practiced other than as specifically described herein.

What is claimed:

1. A method of treating dry eyes over an eight-week cycle of treatments with two visits per week, the method comprising:
    a first visit including (i) intense pulsed light ("IPL") treatment for both eyes where settings are determined by skin pigmentation, susceptibility to sun burn and level of meibomian gland dysfunction ("MGD"), (ii) following the IPL treatment, a low-level light therapy using a blue light for a range of time between 10 and 20 minutes followed by red light for a range of time between 10 and 20 minutes, (iii) following the low-level light therapy, expressing meibomian gland secretions of one or both eye lids, (iv) following the , expressing meibomian gland secretions of eye lids instilling a single drop of proparacaine 1% in a patient's eye, (v) placing a dehydrated amniotic membrane on center of an eye cornea and a bandage contact lens on the eye on top of the dehydrated amniotic membrane or placing a dehydrated amniotic membrane on a concave side of a bandage contact lens and placed on the eye;
    a second visit including (i) low-level light therapy for both eyes using a blue light for a range of time between 10 and 20 minutes followed by red light for a range of time between 10 and 20 minutes, (ii) following the low-level light therapy, expressing meibomian gland secretions of one or both eye lids, (iii) instilling a single drop of proparacaine 1% in a patient's eye, (iv) placing a dehydrated amniotic membrane on center of an eye cornea and a bandage contact lens on the eye on top of the dehydrated amniotic membrane or placing a dehydrated amniotic membrane on a concave side of a bandage contact lens and placed on the eye;
    a third visit including (i) low-level light therapy for both eyes using a blue light for a range of time between 10 and 20 minutes followed by red light for a range of time between 10 and 20 minutes, (ii) following the low-level light therapy, expressing meibomian gland secretions of one or both eye lids, (iii) instilling a single drop of proparacaine 1% in a patient's eye, (iv) placing a dehydrated amniotic membrane on center of an eye cornea and a bandage contact lens on the eye on top of the dehydrated amniotic membrane or placing a dehydrated amniotic membrane on a concave side of a bandage contact lens and placed on the eye;
    a fourth visit including (i) low-level light therapy for both eyes using a blue light for a range of time between 10 and 20 minutes followed by red light for a range of time between 10 and 20 minutes, (ii) following the low-level light therapy, expressing meibomian gland secretions of one or both eye lids, (iii) instilling a single drop of proparacaine 1% in a patient's eye, (iv) placing a dehydrated amniotic membrane on center of an eye cornea and a bandage contact lens on the eye on top of the dehydrated amniotic membrane or placing a dehydrated amniotic membrane on a concave side of a bandage contact lens and placed on the eye;
    a fifth visit including (i) ocular nebulizer treatment for one or both eyes for a range of time between 10 and 20 minutes, (ii) instilling a single drop of proparacaine 1% in a patient's eye, (iv) placing a dehydrated amniotic membrane on center of an eye cornea and a bandage contact lens on the eye on top of the dehydrated amniotic membrane or placing a dehydrated amniotic membrane on a concave side of a bandage contact lens and placed on the eye;
    a sixth visit including (i) ocular nebulizer treatment for one or both eyes for a range of time between 10 and 20 minutes, (ii) instilling a single drop of proparacaine 1% in a patient's eye, (iv) placing a dehydrated amniotic membrane on center of an eye cornea and a bandage contact lens on the eye on top of the dehydrated amniotic membrane or placing a dehydrated amniotic membrane on a concave side of a bandage contact lens and placed on the eye;
    a seventh visit including (i) ocular nebulizer treatment for one or both eyes for a range of time between 10 and 20 minutes, (ii) instilling a single drop of proparacaine 1% in a patient's eye, (iv) placing a dehydrated amniotic membrane on center of an eye cornea and a bandage contact lens on the eye on top of the dehydrated amniotic membrane or placing a dehydrated amniotic membrane on a concave side of a bandage contact lens and placed on the eye; and an eighth visit including (i) ocular nebulizer treatment for one or both eyes for a range of time between 10 and 20 minutes, (ii) instilling a single drop of proparacaine 1% in a patient's eye, (iv) placing a dehydrated amniotic membrane on center of an eye cornea and a bandage contact lens on the eye on top of the dehydrated amniotic membrane or placing a dehydrated amniotic membrane on a concave side of a bandage contact lens and placed on the eye.

2. The method of claim 1, repeating visits one through eight.

\* \* \* \* \*